United States Patent [19]

Chatterjee

[11] 4,020,271

[45] Apr. 26, 1977

[54] CROSSLINKED PHOSPHONOALKYL CELLULOSE AND ABSORBENT DEVICES INCORPORATING SAME

[75] Inventor: Pronoy Kumar Chatterjee, Spotswood, N.J.

[73] Assignee: Personal Products Company, Milltown, N.J.

[22] Filed: Jan. 13, 1975

[21] Appl. No.: 540,368

[52] U.S. Cl. .................................. 536/88; 8/116 P; 8/116.4; 128/285; 128/290 P; 128/296; 536/87

[51] Int. Cl.$^2$ .................. A61F 13/20; C08B 11/00; C08B 15/00

[58] Field of Search ............... 8/116 P, 116.4; 260/231 A; 128/285, 290, 296; 536/87, 88

[56] References Cited

UNITED STATES PATENTS

| | | | |
|---|---|---|---|
| 2,979,374 | 4/1961 | Drake et al. | 8/116 P |
| 3,241,553 | 3/1966 | Steiger | 128/285 |
| 3,811,834 | 5/1974 | Schwemmer et al. | 8/116 P |
| 3,864,076 | 2/1975 | Nachbur et al. | 8/116 P |
| 3,884,628 | 5/1975 | Duffy et al. | 8/116 P |

FOREIGN PATENTS OR APPLICATIONS 2,083,608   1/1972   France ........................ 8/116 R

OTHER PUBLICATIONS

Chemical Abstracts, vol. 77, No. 2, July 10, 1972, p. 7244f.
Chemical Abstracts, vol. 77, No. 18, Oct. 30, 1972, p. 115989m.

*Primary Examiner*—Ronald W. Griffin
*Attorney, Agent, or Firm*—Geoffrey G. Dellenbaugh

[57] ABSTRACT

Alkali metal and ammonium salts of crosslinked phosphonoalkyl cellulose are described which have a phosphorous content of from about 1.5% to about 4.0% by weight and a degree of crosslinking sufficient to make the modified cellulose salts essentially insoluble in aqueous media. These crosslinked phosphonoalkyl cellulose salts have significantly increased fluid absorption capacities as compared to unmodified cellulose and may be incorporated alone or in combination with other absorbent materials into catamenial tampons, sanitary napkins, diapers, and like absorbent devices.

22 Claims, No Drawings

CROSSLINKED PHOSPHONOALKYL CELLULOSE AND ABSORBENT DEVICES INCORPORATING SAME

BACKGROUND OF THE INVENTION

This invention relates to alkali metal and ammonium salts of crosslinked phosphonoalkyl cellulose and to absorbent devices incorporating the same.

Cellulose is often used as an absorbent material in a variety of absorbent devices such as catamenial tampons, sanitary napkins, diapers, and the like. Although cellulose is an adequate absorbent material for many purposes, increased use of disposable absorbent devices has increased the demand for materials which are more absorbent than cellulose. Attention has therefore been directed to techniques for chemically or physically modifying cellulose to increase its absorbency.

One technique which has been used in an attempt to modify cellulose to render it more absorbent is that of substituting ionizable groups for the hydroxyl groups on the anhydroglucose units of cellulose. Such groups render the modified cellulose more absorbent than unmodified cellulose because of their affinity for water, but this affinity also tends to make the modified cellulose more water-soluble than unmodified cellulose. The greater the degree of substitution of the ionizable groups, the greater the degree of water-solubility of the resulting modified cellulose. Finally, the point is reached at which the material is completely soluble in aqueous fluids at ambient temperature and thus useless as an absorbent material. The utility as an absorbent material of substituted cellulose of this type which is otherwise unmodified is severely limited by this increase in solubility.

Thus, while the preparation of phosphonomethyl cellulose was disclosed in Drake, et al., U.S. Pat. No. 2,979,374, the inventors there teach its main utility to be in reducing the combustability of fibers. They disclose that the material becomes readily water-soluble if it contains at least about 2% by weight phosphorous but may also be soluble at lesser concentrations, depending on the form of cellulose used. Because of this solubility of phosphonomethyl cellulose, Drake, et al., do not teach any use thereof as an absorbent material.

It has now been discovered that the undesirable solubility of phosphonoalkyl cellulose (including phosphonomethyl cellulose) in aqueous fluids may be reduced essentially to zero while retaining the desirable absorptivity by crosslinking the phosphonoalkyl cellulose chains. This crosslinked phosphonoalkyl cellulose is essentially insoluble in aqueous fluids and yet has much greater absorbency than unmodified cellulose.

SUMMARY OF THE INVENTION

Crosslinked phosphonoalkyl cellulose celluloe salts may be illustrated by the following:

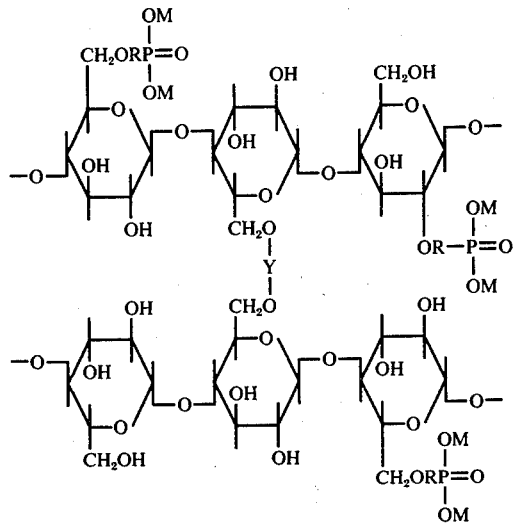

wherein M is an alkali metal ion or ammonium ion (preferably sodium), Y is the residue of a crosslinking agent bifunctional with respect to cellulose (e.g. $-(CH_2)_n$ where n is an integer or

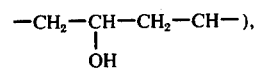

and R is an alkylene radical. If formaldehyde is used as the crosslinking reagent, then Y will be $-(CH_2)n-$; the cellulose is then crosslinked by alkyleneoxy chains. The term "alkylene radical" means a divalent, saturated, aliphatic hydrocarbon of five carbon atoms or less such as, for example, methylene, ethylene, trimethylene, tetramethylene, 1-methyltrimethylene, or the like. Methylene and ethylene are preferred with methylene being most preferred. It should be understood that this formula is intended to illustrate a typical portion of the crosslinked phosphonalkyl cellulose. The substitution of phosphonoalkyl groups

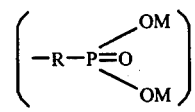

may occur at any of the hydroxyl groups on the anhydroglucose ring of cellulose, and the crosslinking may occur between any of the hydroxyl groups.

There is a desirable relationship between the degree of phosphonoalkylation and the degree of crosslinking in the product of the invention to effect the optimum increase in absorbency consonant with insolubility. It has been found that the degree of phosphonoalkylation should be such that the phosphorous content of the modified cellulose is from about 1.5% to about 4% by weight. The preferred phosphorous content is about 2% by weight. The degree of crosslinking should be sufficient to make the resulting material essentially insoluble in aqueous media and should preferably to from about 0.005 to about 0.190 mole of crosslinking unit (Y in the above figure) per mole of anhydroglucose unit, but the more preferred range is from about 0.015 to about 0.110 mole of cross-linking unit per mole of anhydroglucose unit.

Without crosslinking, phosphonoalkyl cellulose having a phosphorous content in the range described above would either be soluble in aqueous fluids or would disintegrate to such a degree as to be ineffective as an absorbent material.

The crosslinked phosphonoalkyl cellulose salts of the invention may be prepared either by wet crosslinking the cellulose followed by phosphonoalkylation in a separate step or by simultaneously dry crosslinking and phosphonoalkylating the cellulose.

In the former two-step process, the cellulose is treated with a crosslinking reagent solution (described below), washed with water, neutralized with a weak base (if an acid catalyzed reagent is used) or with a weak acid (if a base catalyzed reagent is used), and dried, preferably in an oven at about 100° C. The degree of crosslinking depends on the concentration of the reagent solution and the length of time during which the cellulose is treated therewith. It has been found that treating 40g of cellulose with 500 ml. of a 7% solution of formaldehyde in hydrochloric acid for about 30 minutes produces an acceptable degree of crosslinking. This crosslinking method is well known in the textile art; see for example, Steiger, U.S. Pat. No. 3,241,553. The crosslinked cellulose is then treated with a phosphonoalkylating solution (described below), the excess solution is squeezed out, and the substitution of the phosphonoalkyl groups of the hydroxyl groups on the cellulose is effected by heating the treated cellulose in an oven. The degree of phosphonalkylation is dependent upon the temperature at which this heating is carried out and upon the length of time of the heating. It has been found that heating at about 140° C for about 30 minutes produces an acceptable degree of phosphonalkylation, but clearly one skilled in the art could vary either the temperature or the time (or both) to get acceptable substitution under different conditions. Phosphonalkylation of cellulose is described in the aforementioned Drake, et al., United States Patent. The modified cellulose is finally washed with water and dried, preferably at about 100° C.

In the latter one-step process, the cellulose is first soaked in a crosslinking reagent solution (described below) and the excess squeezed off, and then treated with an excess of Phosphonoalkylating solution (described below), which excess is squeezed off. The treated cellulose is heated as in the two-step process above to effect both crosslinking and phosphonoalkylation, after which the resulting product is washed with water and dried, preferably at about 100° C. This one-step process is simpler than the two-step process and is to be preferred for that reason, although the two-step process allows more independent control of the degree of crosslinking and the degree of phosphonoalkylation.

The cellulose used in either of these processes may be of any type, natural or synthetic, and may be in any form. Thus, wood flour, wood pulp, cotton fibers, and rayon fibers, for example, are all suitable for use in preparing the modified cellulose of the invention. Fibrous cellulose, however, is preferred, with wood pulp being the most preferred material.

While the preferred crosslinking reagent for the two-step wet crosslinking process is formaldehyde and that for the one-step dry crosslinking process is epichlorohydrin or dichloro-2-propanol, any material which is bifunctional with respect to cellulose could be used. Other suitable crosslinking reagents are, for example, dichloroacetic acid, diepoxides (such as butadiene diepoxide), N-methylol acrylamide; divinyl sulfone; bis-epoxypropyl ether; dichloroethane; ethylene glycol-bis-epoxypropyl ether; vinyl cyclohexane dioxide; 1,3-di-(β-hydroxy-Γ-chloropropoxy)-2-propanol; 1,2-di-(β-hydroxy-Γ-chloropropoxy) ethane; 1,2:3,4-diepoxybutane; 1,2:5,6-diepoxyhexane; 2,3-dibromo-1-propanol; 2,3-dichloro-1-propanol; and 2,2'-dichlorethyl ether. All of the above reagents except formaldehyde (which requires an acid catalyst) require an alkaline catalyst such as sodium hydroxide to produce crosslinked cellulose.

The crosslinking reagent solution is a solution of the desired reagent in a suitable solvent such as, for example, water, methanol, ethanol or the like. The concentration of reagent in the solution is generally from about 5% to about 20% by weight.

The phosphonoalkylating reagent solution comprises a basic aqueous solution of a compound of the following structure:

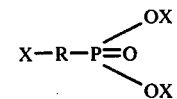

wherein X is a halogen of atomic weight 80 or less and R is an alkylene radical. The preferred reagent is chloromethylphosphonic dichloride.

The crosslinked phosphonoalkyl cellulose of the invention may be used alone or in combination with other absorbent materials in catamenial tampons, sanitary napkins, diapers, and like absorbent devices. The crosslinked phosphonoalkyl cellulose of the invention should be present in at least 5% by weight of the total absorbent material in the absorbent device. The preferred concentration is at least 10% and more preferred is at least 15% by weight.

The present invention will be understood more fully by reference to the following examples.

EXAMPLE I

A crosslinking reagent is prepared by mixing 15 parts by volume of water, 25 parts by volume of concentrated hydrochloric acid, and 10 parts by volume of 35 percent fomaldehyde solution. To 40 grams of southern pine, kraft, bleached wood pulp at room temperature is added 500 milliliters of this crosslinking reagent and the whole is mixed together for 30 minutes. The excess reagent is washed off with water and the remaining acid is neutralized with a 5% solution of sodium bicarbonate. The resulting crosslinked cellulose is dried in an oven at 105° C.

Disodium chloromethyl phosphonate solution is prepared by slowly mixing 35.1 parts by weight of chloromethyl phosphonic dichloride with 96.5 parts by weight of sodium hydroxide which has previously been dissolved in 180 parts by weight of water. The solutions are cooled to 15° C during mixture. The crosslinked cellulose prepared above is treated with this solution in the ratio of one part by weight of crosslinked cellulose to ten parts by weight of disodium chloromethyl phosphonate solution at ambient conditions. The excess reagent is squeezed out and treated fibers are heated in a forced hot-air oven at 140° C for 30 minutes. The product is then thoroughly washed with water and dried in an oven at 105° C. The resulting crosslinked disodium phosphonomethyl cellulose made by this two-step process is insoluble but swellable in both water and saline solution and is a very effective absorbent material.

EXAMPLE II

Southern pine, kraft, bleached wood pulp is soaked in dichloro-2-propanol (20% solution in methanol) for ten minutes and is then squeezed between a two roll padder to remove the excess solution. One part by weight of this wet sample is treated with 19 parts by weight of the disodium chloromethyl phosphonate solution used in the previous example. The excess is squeezed off, and the treated fibers are heated in a forced air oven at 140° C for 30 minutes. The product is then thoroughly washed with water and dried in an oven at 105° C. The resultant crosslinked disodium phosphonomethyl cellulose made by this one-step process is a highly-swellable and effective absorbent material containing 2.1% by weight phosphorous.

EXAMPLE III

The material of Example I is shredded into pulp fluff and combined with varying quantities of unmodified wood pulp fluff. The fluff mixtures are formed into compressed cylindrical tampons having varying densities. Control tampons containing only unmodified wood pulp fluff are also prepared. The capacity of the experimental and control tampons to absorb both pure water and a 1% by weight aqueous sodium chloride solution under simulated in-use conditions is determined by allowing one end of the tampon to be submerged in the fluid to be absorbed for a period of 20 minutes while maintaining the sides of the tampon under a confining pressure of 24 inches of water maintained by enveloping the tampon in a hydraulically inflated polyethylene sleeve. Excess fluid is drained from the tampon, the pressure is released, and the weight of fluid absorbed by the tampon is determined. The tampon capacity in units of volume of fluid absorbed per unit weight of tampon is reported in Table I (water) and Table II (1% NaCl) along with the density of each tampon.

TABLE I

ABSORBENCY OF TAMPONS IN WATER

| Weight Percent of Tampon Filler Components | | Tampon Density g/cc | Tampon Capacity cc/g |
|---|---|---|---|
| Wood Pulp | Crosslinked disodium Phosphonomethyl Cellulose | | |
| 100 | 0 | .44 | 2.68 |
| | | .52 | 2.36 |
| 90 | 10 | .61 | 2.16 |
| | | .80 | 1.95 |
| | | .47 | 3.05 |
| | | .64 | 2.76 |
| 80 | 20 | .95 | 2.40 |
| | | .44 | 3.52 |
| | | .63 | 3.21 |

TABLE I-continued

ABSORBENCY OF TAMPONS IN WATER

| Weight Percent of Tampon Filler Components | | Tampon Density g/cc | Tampon Capacity cc/g |
|---|---|---|---|
| Wood Pulp | Crosslinked disodium Phosphonomethyl Cellulose | | |
| | | .94 | 3.01 |
| 70 | 30 | .37 | 3.94 |
| | | .50 | 3.77 |
| | | .70 | 3.62 |
| 60 | 40 | .38 | 4.20 |
| | | .49 | 4.15 |
| | | .73 | 3.81 |
| 50 | 50 | .40 | 4.69 |
| | | .53 | 4.32 |
| | | .65 | 4.38 |
| | | 1.01 | 4.17 |

TABLE II

ABSORBENCY OF TAMPONS IN 1% SALINE SOLUTION

| Weight Percent of Tampon Filler Components | | Tampon Density g/cc | Tampon Capacity cc/g |
|---|---|---|---|
| Wood Pulp | Crosslinked disodium Phosphonomethyl Cellulose | | |
| 100 | 0 | .26 | 3.30 |
| | | .40 | 2.58 |
| | | .54 | 2.47 |
| | | .67 | 2.02 |
| | | .87 | 1.79 |
| 50 | 50 | .26 | 4.00 |
| | | .39 | 4.09 |
| | | .54 | 3.93 |
| | | .67 | 3.72 |
| | | .97 | 3.64 |
| 0 | 100 | .26 | 5.40 |

EXAMPLE IV

The procedure of Example III was followed except that all tampons were compressed to 0.4 g/cc density. The capacity of each tampon is reported in Table III, along with the present improvement over untreated wood pulp based on the absorbency of a 100% wood pulp tampon.

For comparison, a similar tampon comprising 50% crosslinked but otherwise unmodified cellulose made in accordance with the teaching of the aforementioned Steiger United States Patent and 50% untreated cellulose exhibited a percentage improvement of only 3.9% in water and only 7.5% in saline solution. Thus, it is clear that the crosslinking contributes only incidentally to the increased absorbency of the product of the invention.

TABLE III

ABSORBENCY OF TAMPONS COMPRESSED TO 0.4 g/cc DENSITY

| Weight Percent Disodium Crosslinked Phosphonomethyl Cellulose in Tampon Filler | Capacity in Water | | Capacity in 1% Saline Solution | |
|---|---|---|---|---|
| | cc/g | % Improvement over Untreated | cc/g | % Improvement over Untreated |
| 0 | 2.80 | — | 2.65 | — |
| 10 | 3.27 | 16.8 | | |
| 20 | 3.61 | 28.9 | | |
| 30 | 3.89 | 38.9 | | |
| 40 | 4.20 | 50.0 | | |
| 50 | 4.62 | 65.0 | 4.09 | 54.3 |

While the invention has been discussed above by reference to various specific examples, it should be understood that many embodiments are within the scope of the present invention, which scope is not to be limited except by the appended claims.

What is claimed is:

1. A crosslinked phosphonoalkyl cellulose having a degree of crosslinking sufficient to make said cellulose essentially insoluble in aqueous media, said cellulose containing

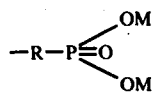

groups wherein R is an alkylene radical of no more than 5 carbon atoms and wherein M is a member selected from the group consisting of alkali metal ions and ammonium ions, said cellulose containing from about 1.5% to about 4.0% phosphorous by weight.

2. A crosslinked phosphonoalkyl cellulose as described in claim 1 wherein R is a member selected from the group consisting of methylene and ethylene.

3. A crosslinked phosphonoalkyl cellulose as described in claim 2 which has a degree of crosslinking from about 0.005 to about 0.190 mole of crosslinking unit per mole of anhydroglucose unit.

4. A crosslinked phosphonoalkyl cellulose as described in claim 2 which is crosslinked by alkyleneoxy chains.

5. A crosslinked phosphonoalkyl cellulose as described in claim 1 wherein R is methylene and M is sodium.

6. A crosslinked phosphonomethyl cellulose as described in claim 5 wherein said cellulose contains about 2% phosphorous by weight.

7. A crosslinked phosphonomethyl cellulose as described in claim 5 which has a degree of crosslinking of from about 0.015 to about 0.110 mole of crosslinking unit per mole of anhydroglucose unit.

8. A crosslinked phosphonoalkyl cellulose as described in claim 1 which is fibrous.

9. A crosslinked phosphonoalkyl cellulose as described in claim 3 which is fibrous.

10. A crosslinked phosphonomethyl cellulose as described in claim 6 which is fibrous.

11. An absorbent product having an absorbent mass comprising at least about 10% of the crosslinked phosphonoalkyl cellulose of claim 1.

12. An absorbent product having an absorbent mass comprising at least about 5% of the crosslinked phosphonomethyl cellulose of claim 6.

13. An absorbent product having an absorbent mass comprising at least about 10% of the crosslinked phosphonomethyl cellulose of claim 6.

14. An absorbent product having an absorbent mass comprising at least about 5% of the crosslinked phosphonomethyl cellulose of claim 10.

15. A sanitary napkin comprising at least about 5% of the crosslinked phosphonoalkylcellulose of claim 1.

16. A sanitary napkin comprising at least about 5% of the crosslinked phosphonomethyl cellulose of claim 10.

17. A diaper comprising at least about 5% of the crosslinked phosphonoalkyl cellulose of claim 1.

18. A diaper comprising at least about 5% of the crosslinked phosphonomethyl cellulose of claim 10.

19. A catamenial tampon comprising at least about 5% of the crosslinked phosphonoalkyl cellulose of claim 1.

20. A catamenial tampon comprising at least about 5% of the crosslinked phosphonomethyl cellulose of claim 10.

21. An absorbent product having an absorbent mass comprising at least about 5% by weight crosslinked phosphonoalkyl cellulose having a degree of crosslinking sufficient to make said crosslinked phosphonoalkyl cellulose essentially insoluble in aqueous media, said crosslinked phosphonoalkyl cellulose containing

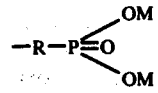

groups wherein R is an alkylene radical of no more than 5 carbon atoms and wherein M is a member selected from the group consisting of alkali metal ions and ammonium ions, said crosslinked phosphonoalkyl cellulose containing from about 1.5% to about 4.0% phosphorous by weight, and said crosslinked phosphonoalkyl cellulose having significantly greater fluid absorption capacity than unmodified cellulose.

22. An absorbent product having an absorbent mass comprising at least about 15% by weight crosslinked phosphonoalkyl cellulose having a degree of crosslinking sufficient to make said crosslinked phosphonoalkyl cellulose essentially insoluble in aqueous media, said crosslinked phosphonoalkyl cellulose containing

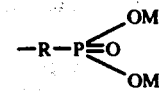

groups wherein R is an alkylene radical of no more than 5 carbon atoms and wherein M is a member selected from the group consisting of alkali metal ions and ammonium ions, said crosslinked phosphonoalkyl cellulose containing from about 1.5% to about 4.0% phosphorous by weight, and said crosslinked phosphonoalkyl cellulose having significantly greater fluid absorption capacity than unmodified cellulose.

* * * * *

UNITED STATES PATENT AND TRADEMARK OFFICE
CERTIFICATE OF CORRECTION

PATENT NO. : 4,020,271
DATED : April 26, 1977
INVENTOR(S) : Pronoy Kumar Chatterjee It is certified that error appears in the above-identified patent and that said Letters Patent are hereby corrected as shown below:

In Column 1, line 67, "cellulose celluloe salts" should read ---cellulose salts---

In Column 2, line 31, "—(CH$_2$)n-;" should read "-(CH$_2$)$_{\bar{n}}$;"

In Column 2, line 40, "phosphonalkyl" should read ---phosphonoalkyl---

In Column 2, line 63, "preferably to from about" should read ---preferably be from about---

In Column 4, line 59, "mixture" should read ---mixing---

Signed and Sealed this

Twenty-first Day of February 1978

[SEAL]

Attest:

RUTH C. MASON
*Attesting Officer*

LUTRELLE F. PARKER
*Acting Commissioner of Patents and Trademarks*